United States Patent
Khan et al.

(10) Patent No.: US 7,740,665 B2
(45) Date of Patent: Jun. 22, 2010

(54) SINGLE COMPONENT HAIR COLORING COMPOSITION

(75) Inventors: Zubaida Khan, Stamford, CT (US); Marina Azizova, New Canaan, CT (US); Rushi Tasker, Trumbull, CT (US)

(73) Assignee: Zotos International, Inc., Darien, CT (US)

( * ) Notice: Subject to any disclaimer, the term of this patent is extended or adjusted under 35 U.S.C. 154(b) by 101 days.

(21) Appl. No.: 12/283,827

(22) Filed: Sep. 15, 2008

(65) Prior Publication Data

US 2010/0064449 A1   Mar. 18, 2010

(51) Int. Cl.
*A61Q 5/10* (2006.01)
(52) U.S. Cl. .................. 8/405; 8/406; 8/524; 8/552; 8/553; 8/617; 8/649
(58) Field of Classification Search .................... 8/405, 8/406, 524, 552, 553, 617, 649
See application file for complete search history.

(56) References Cited

U.S. PATENT DOCUMENTS

2009/0151087 A1*   6/2009   Mario et al. ................... 8/406

* cited by examiner

*Primary Examiner*—Eisa B Elhilo
(74) *Attorney, Agent, or Firm*—Melvin I. Stoltz

(57) ABSTRACT

By combining a hydrogen peroxide liberating complex with hair coloring dyes, a highly effective hair coloring composition is obtained which comprises a stable dry powder composition which can be stored in a single container. When use is desired, the stable dry powder composition of the present invention is mixed with water, activating the liberation of hydrogen peroxide and allowing the desired hair coloring effect to be achieved. In addition to providing a single stable dry powder formulation, the composition of the present invention is capable of achieving a wide array of shades and coloring effects.

19 Claims, No Drawings

SINGLE COMPONENT HAIR COLORING COMPOSITION

TECHNICAL FIELD

This invention relates to hair coloring compositions and, more particularly, to single component hair coloring compositions.

BACKGROUND ART

Throughout the years, there has been a desire to alter the color of synthetic and natural fibers. In particular, coloring of human hair has been sought in view of changing styles and fashion. However, due to the inherent composition of hair fiber, and the chemical and mechanical exposure encountered by the hair fibers during normal care and styling, obtaining and maintaining a precise color has been an illusive goal that requires constant improvements in technology.

As is well known, hair is composed of a unique protein material called "keratin" which is repeatedly being subjected to both chemical and mechanical damage from combing and brushing, as well as from sunlight, chlorinated water, shampooing, permanent waving, and other such treatments involving various chemicals. As a result, depending upon the length of the hair fiber, the distal ends of each hair fiber tend to have substantially more damage than the proximal ends nearer to the scalp. This inconsistency may cause variation in the dye uptake by the hair fiber, resulting in color variations along the length of the hair fiber.

In spite of the long history with the coloration of hair and the extensive effort that has been expended in attempting to eliminate the problems associated with the dyeing of human hair, no system has been achieved which is capable of overcoming all of the drawbacks and difficulties encountered with hair dyes. Included among these drawbacks is the need for a two component system in permanent hair coloring technology.

Temporary dyes or hair colors last through a few shampooings, while semi-permanent hair colors are retained for three to six weeks of shampooings. The permanent dyes or colors, which are often equally employable on plant derived and synthetic fibers, as well as hair keratin, cannot be shampooed out from hair fibers.

In virtually all prior art, using permanent hair dyes requires hydrogen peroxide along with the particular dyestuffs. During the application, the mixture enters into the hair fibers and reacts therein to form larger dyes of a predetermined color. Since the dye molecules formed are larger than the molecules entering the hair fibers, the formed dyes are trapped within the hair fibers, and are unable to diffuse out of the fibers. Consequently, the resulting coloring is trapped within the hair fiber and is permanent.

One advantage that has been found from using these types of dye mixtures is the ability to lighten hair, since the presence of both hydrogen peroxide and the alkaline environment of the mixture will also remove natural hair color, which is then replaced by the colors formed in situ.

One problem which is typically encountered in virtually all prior art permanent hair coloring compositions is a requirement that the hair color and peroxide must be distributed as two components, in two separate and independent containers. Both components require suitable and often costly containers and have to be additionally housed in the outer box. One container is employed for storing the hair dye precursors and alkali, while the second container is employed for storing hydrogen peroxide, which is unstable at high pH. When actual use of the hair coloring composition is desired, the contents of the two containers are intermixed and immediately applied to the hair fibers. The unused color needs to be wasted since all of the dye stuff has reacted.

In addition to being less expensive, a single container can have a number of advantages. Traditional oxidative hair color is sold in single applications. A single container hair color can be used for multiple applications and can dramatically minimize the amount of wasted color. Another commercial problem is inability to sample consumers with hair color prior to purchase, since the two-container package is expensive. Single containers can be offered in a small packet as a sample.

Although some prior art hair dyeing compositions purport to provide a single component system, these prior art systems employ urea, sodium phosphate, citric acid, and/or sodium carbonate perhydrates or percarbonates as lightening and oxidizing ingredients. These materials, commonly used in bleaching, give more damage to hair than traditional hydrogen peroxide lighten-ers. There are no products presently available in this field which employ hydrogen peroxide liberating compounds which are safe to handle and readily mix with water to give the desired hair color and composition achieved by the present invention.

Therefore, it is a principal object of the present invention to provide a permanent or long-lasting dye composition for use on human hair which effectively achieves a single component system comprising stable dry powder, which is storable in a single container and is easily used and safely handled by an operator for achieving a desired hair coloring effect.

Another object of the present invention is to provide a permanent or long lasting dye composition for use on human hair which is capable of being easily and successfully employed on all desired hair fibers with consistent, repeatable and predictable coloration results.

A further object of the present invention is to provide a permanent dye composition having the characteristic features described above which is long lasting and durable color, incapable of being washed from the fibers.

Other and more specific objects will in part be obvious and will in part appear hereinafter.

DETAILED DESCRIPTION

By employing the present invention, the prior art failings and drawbacks mentioned above are overcome, and a highly effective, hair coloring composition is obtained which comprises a stable dry powder composition stored in a single container. When use is desired, the stable dry powder composition of the present invention is mixed with warm water, activating the liberation of hydrogen peroxide and allowing the desired hair coloring effect to be achieved.

In addition to providing a single stable dry powder formulation, the composition of the present invention is capable of achieving a wide array of shades ranging from blonde to dark brown and black, and red and gold tones and blue and blue violet tones based upon the choice of permanent and semi-permanent dyes. Furthermore, the composition of the present invention pro-vides the desired viscosity and alkaline pH for application to hair fibers.

In accordance with the present invention, the hair coloring composition comprises a stable, dry powder formulation formed as a single part for application to the hair, with the principal components of the composition comprising between about 0.10% and 10% by weight based upon the weight of the entire composition of the desired hair coloring dyes, and between about 10% and 80% by weight based upon the weight of the entire composition of a hydrogen peroxide liberating complex. The hydrogen peroxide liberating complex, also called plasdone hydrogen peroxide complex consists of hydrogen peroxide and polyvinylpyrrolidone polymer (also called 2-pyrrolidinone, 1-ethenyl homopolymer)

In addition, in the preferred composition, non-aqueous additives are incorporated into the final composition. Preferably, these additives comprise one or more selected from the group consisting of alkalis, such as an ammonia liberator or sodium silicate, powder thickeners, such as xanthan gum, antioxidants, chelating agents, pH buffering agents, and permanent hair dye precursors.

In the preferred composition, the hair coloring dyes comprise one or more oxidative dyes selected from the group consisting of p-phenyelenediamine, p-phenylenediamine sulfate, p-aminophenol, p-aminophenol sulfate, m-aminophenol, m-aminophenol sulfate, N—N-bis 2-hydroxyethyl p-phenyelenediamine sulfate, 4-Amino-m-Cresol, phenyl methylpyrazolone, 5-amino-6-chloro-o-cresol, 1-naphthol, 4-amino, 2-hydroxytoluene, 2-amino, 3-hydroxypyridine, resorcinol, 2-methyl resorcinol, 2-amino-4-hydroxyethyl amino anisole sulfate, 2-amino-6-chloro-4-nitrophenol.

In addition, if desired, the hair coloring dyes may comprise one or more direct dyes selected from the group consisting of Basic Red 51, Basic Yellow 87, Basic Yellow 57, Basic Blue 99, Basic Green 1, Basic Violet 2, Red 33, Basic Orange 31, Basic Violet 4, Basic Blue 9, Basic Blue 3, Basic Red 3, Basic Red 76, Basic Brown 17, 3-nitro-p-hydroxyethyl aminophenol, HC Red No. 3, HC Yellow No. 2, HC Yellow No. 4, N,N'-Bis(2hydroxyethyl) 2-nitro-p-phenylenediamine.

In addition, it has also been found that by incorporating up to 20% by weight based upon the weight of the entire composition of a thickener, the resulting mixture achieved, after the addition of water, comprises a viscosity which is appropriate for coloring hair. In this regard, thickeners, such as xanthan gum may be employed, for an easy application hair dye composition.

In the preferred composition, up to 14% by weight based upon the weight of the entire composition of a powder alkali is incorporated therein. Although any suitable powder alkali can be employed, it has been found that one or more selected from the group consisting of sodium hydroxide, sodium silicate, percarbonate, perborate, and perchlorate are preferred.

In accordance with the present invention, the hydrogen peroxide liberating complex preferably comprises between about 100% and 25% by weight based upon the weight of the entire composition of hydrogen peroxide within a polyvinylpyrrolidone polymer. Furthermore, the hydrogen peroxide liberating complex is also constructed to yield between about 0.10% and 14% by weight based upon the weight of the entire composition of peroxide when the composition is mixed with water. It has been found that by employing these parameters, a highly effective single part hair color composition is realized which is easily employed and provides the desired hair coloring effects.

BEST MODE FOR CARRYING OUT THE INVENTION

In order to demonstrate the efficacy of the present invention and the achievement of a hair dye or hair color composition which comprises a stable dry powder composition stored in a single container and, when mixed with warm water, produces a permanent hair coloring effect, a plurality of alternate compositions were manufactured in accordance with the present invention and tested as detailed below. The following examples are presented in order to fully demonstrate the highly effective hair dye and hair coloring compositions of the present invention and the substantially enhanced results achieved thereby.

By reviewing the following examples, the ability of the hair dye or hair coloring compositions of the present invention to provide the desired results is clearly established. However, it is to be understood that the following examples are intended as a teaching of the best mode for carrying out the present invention and are not intended to limit the breadth of this discovery.

In each of the following examples, alternate formulations made in accordance with the present invention are fully detailed. In each instance, the particular formulation was mixed with warm water, having a temperature ranging between about 33° C. and 38° C. In addition, each composition was mixed with warm water in an equal ratio (1:1) just prior to dyeing the hair fibers. Once the dyeing process was completed, the color obtained it was noted and is provided below in association with each formulation.

Example I

Powder Hair Dye Composition

| CHEMICAL NAME | Weight % |
| --- | --- |
| Sodium Silicate | 15.47 |
| Sodium Sulfate | .442 |
| Polyvinylpyrrolidone and Peroxide | 72.93 |
| P-Phenylene Diamine Sulfate | 4.42 |
| M-Aminophenol Sulfate | 1.66 |
| Disodium Ethylene Diamine Tetraacetate | .442 |
| Xanthum Gum | 4.42 |
| Sodium Sulfite | .221 |

The above mixture was mixed with warm water (33° C.-38° C.) in equal ratios (1:1) prior to dyeing the hair. The resultant color on hair was brown shade.

Example II

Powder Hair Dye Composition

| CHEMICAL NAME | Weight % |
| --- | --- |
| Sodium Silicate | 15.25 |
| Sodium Sulfate | .436 |
| Polyvinylpyrrolidone and Peroxide | 71.87 |
| Disodium Ethylene Diamine Tetraacetate | .436 |
| Xanthan Gum | 4.36 |
| P-aminophenol Sulfate | 3.92 |
| 2-Amino-4-Hydroxyethyl Aminoanisole Sulfate | 2.1878 |
| P-amino-Cresol | 1.31 |
| Sodium Sulfite | .22 |

The above mixture was mixed with warm water (33° C.-38° C.) in equal ratios (1:1) prior to dyeing hair. The resultant color on hair was Red Violet shade.

Example III

Powder Hair Dye Composition

| CHEMICAL NAME | Weight % |
| --- | --- |
| Sodium Silicate | 15.89 |
| Sodium Sulfate | .45 |
| Polyvinylpyrrolidone and Peroxide | 74.90 |
| Sodium Sulfite | .227 |
| Disodium Ethylene Diamine Tetraacetate | .45 |
| Xanthan Gum | 4.54 |
| Basic Orange 31 | .227 |
| 2-Amino-6-Chloro-4-Nitrophenol | 1.36 |
| P-aminophenol Sulfate | .91 |
| 4-Amino-2-Hydroxytoluene | .91 |
| M-Aminophenol Sulfate | .114 |

The above mixture was mixed with warm water (33° C.-38° C.) in equal ratios (1:1) prior to dyeing hair. The resultant color on hair was Red Orange shade.

Example IV

Powder Hair Dye Composition

| CHEMICAL NAME | Weight % |
| --- | --- |
| Sodium Silicate | 15.155 |
| Sodium Sulfate | .433 |
| Polyvinylpyrrolidone and Peroxide | 71.445 |
| P-Phenylene Diamine Sulfate | 6.28 |
| M-aminophenol Sulfate | 1.73 |
| 2-Amino-4-Hydroxyethyl Aminoanisole Sulfate | 2.1878 |
| Disodium Ethylene Diamine Tetraacetate | .433 |
| Xanthan Gum | 4.33 |
| Sodium Sulfite | .217 |

The above mixture was mixed with warm water (33° C.-38° C.) in equal ratios (1:1) prior to dyeing hair. The resultant color on hair was Brown shade.

Example V

Powder Hair Dye Composition

| CHEMICAL NAME | Weight % |
| --- | --- |
| Sodium Silicate | 16.17 |
| Sodium Sulfate | .462 |
| Polyvinylpyrrolidone and Peroxide | 76.23 |
| P-aminophenol Sulfate | 1.155 |
| Resorcinol | .231 |
| P-aminophenol Sulfate | 3.92 |
| Disodium Ethylene Diamine Tetraacetate | .45 |
| Xanthan Gum | 4.62 |
| Sodium Sulfite | 0.231 |

The above mixture was mixed with warm water (33° C.-38° C.) in equal ratios (1:1) prior to dyeing hair. The resultant color on hair was a Golden Blonde shade.

Example VI

Powder Hair Dye Composition

| CHEMICAL NAME | Weight % |
| --- | --- |
| Potassium Persulfate | 10.44 |
| Ammonium Persulfate | 7.41 |
| Sodium Metasilicate | 4.72 |
| Sodium Silicate | 13.48 |
| Sodium Stearate | 1.85 |
| Hydroxyethylcellulose | 1.18 |
| Xanthan Gum | 1.68 |
| Hydrated Silica | 1.21 |
| Aluminum Stearate | 0.74 |
| Disodium Ethylene Diamine Tetraacetate | 0.51 |
| Silica | .084 |
| Polyvinylpyrrolidone and Peroxide | 55.59 |
| Sodium Sulfate | 0.34 |

To the above mixture, warm water (33° C.-38° C.) was added in 1:1 ratios and was mixed well before applying to the hair for thirty minutes. Results were equal to bleaching effect on brown hair which was treated with bleach powder mixed with 20 volume peroxide for thirty minutes.

It will thus be seen that the objects set forth above, among those made apparent from the preceding description, are efficiently attained and, since certain changes may be made in the above compositions, it is intended that all matter contained in the above description shall be interpreted as illustrative and not limiting.

It is also to be understood that the following claims are intended to cover all of the generic and specific features of the invention herein described and all statements of the scope of the invention which, as a matter of language, might be said to fall therebetween.

In particular, it is to be understood that in said claims, ingredients or compounds recited in the singular are intended to include compatible mixtures of such ingredients whenever the sense permits.

Having described our invention what we claim as new and desire to secure by Letters Patent is:

1. A hair coloring composition formed as a dry powder storable in a single container prior to use and comprising:
   A. between about 0.1% and 10% by weight based upon the weight of the entire composition of hair coloring dyes comprising oxidative dyes and direct dyes;
   B. between about 10% and 80% by weight based upon the weight of the entire composition of a hydrogen peroxide liberating complex; and
   C. non-aqueous additives forming the balance.

2. The hair coloring composition defined in claim 1, wherein the hydrogen peroxide liberating complex is further defined as comprising polyvinyl-pyrrolidone and hydrogen peroxide polymers.

3. The hair coloring composition defined in claim 1, wherein the hydrogen peroxide liberating complex is further defined as comprising between about 10% and 25% by weight based upon the weight of the entire complex of hydrogen peroxide encompassed within the polyvinylpyrrolidone polymer.

4. The hair coloring composition defined in claim 1, wherein the hydrogen peroxide liberating complex is further defined as being capable of releasing between about 0.1% and 14% by weight based upon the weight of the entire complex of peroxide when intermixed with water.

5. The hair coloring composition defined in claim 1, wherein the hydrogen peroxide liberating complex is further defined as comprising 1-ethenyl-pyrrolidinone, homo polymer and hydrogen peroxide, or plasdone hydrogen peroxide complex.

6. The hair coloring composition defined in claim 1, wherein the non-aqueous additives are further defined as comprising one or more compounds selected from the group consisting of alkalis, thickeners, antioxidants, chelating agents, and pH buffering agents.

7. The hair coloring composition defined in claim 1, wherein said oxidative dyes selected from the group consisting of p-phenyelenediamine, p-phenylenediamine sulfate, p-aminophenol, p-aminophenol sulfate, m-aminophenol, m-aminophenol sulfate, N—N-bis 2-hydroxyethyl p-phenyelenediamine sulfate, 4-Amino-m-Cresol, phenyl methylpyrazolone, 5-amino-6-chloro-o-cresol, 1-naphthol, 4-amino-2-hydroxytoluene, 2-amino, 3-hydroxypyridine, resorcinol, 2-methyl resorcinol, 2-amino-4-hydroxyethyl amino anisole sulfate, and 2-amino-6-chloro-4-nitrophenol.

8. The hair coloring composition defined in claim 1, wherein said direct dyes selected from the group consisting of Basic Red 51, Basic yellow 87, Basic yellow 57, Basic blue 99, Basic green 1, Basic Violet 2, Red 33, Basic Orange 31, Basic Violet 4, Basic blue 9, Basic blue 3, Basic Red 3, Basic Red 76, Basic Brown 17, 3-nitro-p-hydroxyethyl aminophenol, HC Red No. 3, HC Yellow No. 2, HC Yellow No. 4, and N,N'-Bis(2hydroxyethyl) 2-nitro-p-phenylenediamine.

9. The hair coloring composition defined in claim 1, wherein the additive comprises up to 20% by weight based upon the weight of the entire composition of a thickener.

10. The hair coloring composition defined in claim 9, wherein said thickener comprises Xanthan gum.

11. The hair coloring composition defined in claim 1, wherein the additive comprises up to 14% by weight based upon the weight of the entire composition of a powder alkali comprising one or more compounds selected from the group consisting of sodium hydroxide, sodium silicate, percarbonate, perborate, and perchlorate.

12. The hair coloring composition defined in claim 1, wherein said composition is intermixed with water in a 1:1 equal ratio immediately prior to use to produce a hair coloring composition having a pH ranging between about 5 and 12.

13. The hair coloring composition defined in claim 1, wherein said composition is stored as a dry powder in a single container until use is desired.

14. A method for coloring hair comprising the steps of:
A. forming a hair coloring composition comprising:
   a) between 0.1% and 10% by weight based upon the weight of the entire composition of hair coloring dyes comprising oxidative dyes and direct dyes;
   b) between 10% and 80% by weight based upon the weight of the entire composition of a hydrogen peroxide liberating complex; and
   c) non-aqueous additives forming the balance;
B. maintaining the hair coloring composition as a stable dry powder in a single container until use is desired;
C. intermixing the hair coloring composition with an equal part of water prior to use; and
D. thoroughly applying the hair dyeing composition to the hair fibers and washing it off after prescribed time to produce the desired hair color.

15. The method for coloring hair defined in claim 14, wherein said water is further defined as comprising a temperature ranging between about 33° C. and 38° C.

16. The method for coloring hair defined in claim 14, wherein the hydrogen peroxide liberating complex is further defined as comprising between 10% and 25% by weight based upon the weight of the entire complex of hydrogen peroxide encompassed within a polyvinylpyrrolidone polymer.

17. The method for coloring hair defined in claim 14, wherein the hair coloring dyes are further defined as comprising one or more oxidative dyes selected from the group consisting of p-phenyelenediamine, p-phenylenediamine sulfate, p-aminophenol, p-aminophenol sulfate, m-aminophenol, m-aminophenol sulfate, N—N-bis 2-hydroxyethyl p-phenyelenediamine sulfate, 4-amino-m-Cresol, phenyl methylpyrazolone, 5-amino-6-chloro-o-cresol, 1-naphthol, 4-amino-2-hydroxytoluene, 2-amino, 3-hydroxypyridine, resorcinol, 2-methyl resorcinol, 2-amino-4-hydroxyethyl amino anisole sulfate, and 2-amino-6-chloro-4-nitrophenol.

18. The method for coloring hair defined in claim 14, wherein the hair coloring dyes are further defined as comprising one or more direct dyes selected from the group consisting of Basic Red 51, Basic Yellow 87, Basic Yellow 57, Basic Blue 99, Basic Green 1, Basic Violet 2, Red 33, Basic Orange 31, Basic Violet 4, Basic Blue 9, Basic Blue 3, Basic Red 3, Basic Red 76, Basic Brown 17, 3-nitro-p-hydroxyethyl aminophenol, HC Red No. 3, HC Yellow No. 2, HC Yellow No. 4, and N,N'-Bis(2hydroxyethyl) 2-nitro-p-phenylenediamine.

19. The method for coloring hair defined in claim 14, wherein said additives are further defined as comprising one or more compounds selected from the group consisting of alkalis, thickeners, antioxidants, chelating agents, pH buffering agents, and permanent hair dye precursors.

* * * * *